United States Patent [19]

Uneme et al.

[11] Patent Number: 5,438,065

[45] Date of Patent: Aug. 1, 1995

[54] DIAMINOETHYLENE COMPOUNDS

[75] Inventors: Hideki Uneme, Osaka; Isao Minamida, Kawabe; Tetsuo Okauchi, Hirakata, all of Japan

[73] Assignee: Takeda Chemical Industries, Osaka, Japan

[21] Appl. No.: 507,776

[22] Filed: Apr. 12, 1990

[30] Foreign Application Priority Data

Apr. 14, 1989 [JP] Japan .................. 1-95580
Aug. 2, 1989 [JP] Japan .................. 1-201980

[51] Int. Cl.$^6$ .................. A61K 31/44; C07D 213/38
[52] U.S. Cl. .................. 514/353; 514/344; 514/357; 514/365; 514/370; 546/289; 546/300; 546/306; 546/330; 546/332
[58] Field of Search .............. 546/289, 306, 330, 332; 514/344, 353, 357, 365, 370; 548/205

[56] References Cited

FOREIGN PATENT DOCUMENTS 0302389 2/1989 European Pat. Off. .

OTHER PUBLICATIONS

Banks, James E., *Naming Organic Compounds* 1976 (Saunders College Publishing) p. 246.

*Primary Examiner*—Bernard Dentz
*Attorney, Agent, or Firm*—Foley & Lardner

[57] ABSTRACT

Diaminoethylene derivatives of the formula:

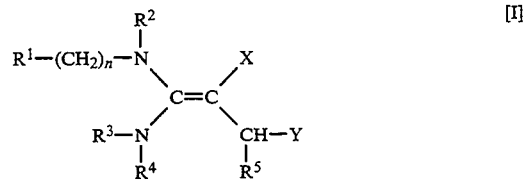

wherein $R^1$ is a heterocyclic group which may be substituted, $R^2$, $R^3$ and $R^4$ are a hydrogen atom or a hydrocarbon group which may be substituted or $R^3$ and $R^4$ are combined to form a cyclic amino group together with the adjacent nitrogen atom; $R^5$ is hydrogen atom or a hydrocarbon group or heterocyclic group which may be substituted; X is an electron attractive group; Y is a hydroxyl or substituted hydroxyl group, amino or substituted amino group or mercapto or substituted mercapto group; n is 0 or 1; or their salts, which are useful as insecticides.

21 Claims, No Drawings

DIAMINOETHYLENE COMPOUNDS

BACKGROUND OF THE INVENTION

1. Field of the Invention

This invention relates to diaminoethylene derivatives and their salts, processes for preparing the same and insecticidal compositions containing them.

2. Description of the Prior Art

Various kinds of synthesized compounds such as organic phosphoric esters, carbamic esters or pyrethroid compounds possessing an effect of controlling harmful insects have been used as insecticides. Repeated use of such a limited group of compounds causes a harmful influence such as increase of resistance of insects against insecticides, and actually raises serious problems in every place. Although some of the above insecticides possess a strong activity, they are not always satisfactory because they have high toxicity against human beings, beasts and fishes and occasionally against natural enemies of insects, and a high residual property in soil or the like.

SUMMARY OF THE INVENTION

This invention is intended for providing diaminoethylene compounds which possess low toxicity against human beings, beasts, fishes and natural enemies and also possess superior effects against insects, processes for preparation thereof and insecticidal compositions containing those compounds.

Thus, this invention provides diaminoethylene compounds of the following formula [I] (hereinafter sometimes called "diaminoethylene compound(s) [I]" or "compound(s) [I]") and their salts

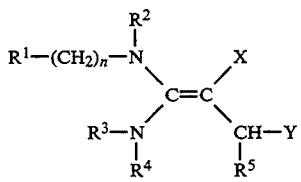

wherein $R^1$ is a heterocyclic group which may be substituted; $R^2$, $R^3$ and $R^4$ may be the same or different, and are a hydrogen atom or a hydrocarbon group which may be substituted, or $R^3$ and $R^4$ are combined to form a cyclic amino group with the adjacent nitrogen atom; $R^5$ is a hydrogen atom, a hydrocarbon group which may be substituted or a heterocyclic group which may be substituted; n is 0 or 1; X is an electron attractive group; Y is a group of the formula —$OR^6$ (in which $R^6$ is a hydrogen atom, a hydrocarbon group which may be substituted or a heterocyclic group which may be substituted), a group of the formula —$NR^7R^8$ (in which $R^7$ and $R^8$ are, the same or different, a hydrogen atom or a hydrocarbon group which may be substituted, or $R^7$ and $R^8$ are combined to form a cyclic amino group with the adjacent nitrogen atom), or a group or the formula —$S(O)_mR^9$ (in which $R^9$ is a hydrocarbon group which may be substituted or a heterocyclic group which may be substituted and m is 0, 1 or 2).

This invention also provides processes for preparing the diaminoethylene compounds [I] and salts thereof which comprises (a) reacting a compound of the formula [II]:

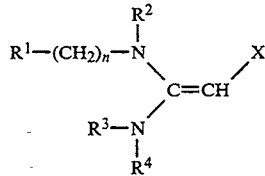

wherein each symbol has the same meaning as above, (hereinafter sometimes referred to as "compound(s) [II]") or its salt with a compound of the formula [III]:

wherein $R^5$ has the same meaning as above, (hereinafter sometimes referred to as "compound(s) [III]")
to give a diaminoethylene compound of the formula [$I^a$]:

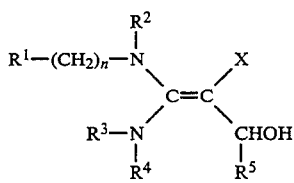

wherein each symbol has the same meaning as above or its salt, or (b) reacting a compound [II] or its salt with a compound [III] and a compound of the formula [IV]:

wherein $Y^a$ has the same meaning as Y provided that $Y^a$ is not hydroxyl group
to give a diaminoethylene compound of the formula [$I^b$]:

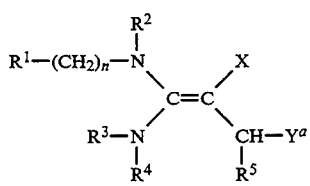

wherein each symbol has the same meaning as above or its salt, or (c) (i) reacting a compound of the formula [V]:

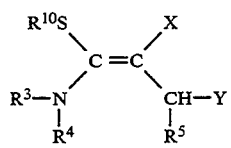

wherein each of $R^3$, $R^4$, $R^5$, X and Y has the same meaning as above, and $R^{10}$ is a lower alkyl group or its salt with a compound of the formula [VI]:

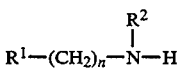 [VI]

wherein each symbol has the same meaning as above or its salt, or
(ii) reacting a compound of the formula [VII]:

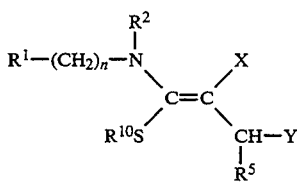 [VII]

wherein each symbol has the same meaning as above or its salt with a compound of the formula [VIII]:

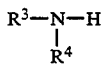 [VIII]

wherein each symbol has the same meaning as above or its salt
to give a diaminoethylene compound [I] or its salt, or
(d) oxidizing a compound of the formula [$I^c$]:

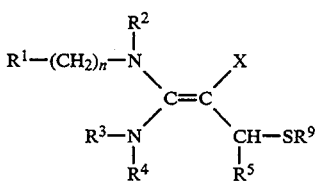 [$I^c$]

wherein each symbol has the same meaning as above or its salt
to give a diaminoethylene compound of the formula [$I^d$]:

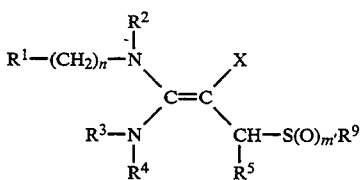 [$I^d$]

wherein each of $R^1$, $R^2$, $R^3$, $R^4$, $R^5$, $R^9$, n and X has the same meaning as above, and m' is 1 or 2 or its salt.

Further, it provides an insecticidal composition containing the diaminoethylene compound [I] or its salt.

PREFERRED EMBODIMENTS OF THE INVENTION

The heterocyclic group of the "heterocyclic group which may be substituted" represented by $R^1$, $R^5$, $R^6$ and $R^9$ in the above formulas includes a 5- to 8-membered, preferably 5- to 6-membered ring containing 1 to 5 hetero atoms, preferably 1 to 3 hetero atoms such as oxygen atom, sulfur atom and nitrogen atom, or its condensed ring. Specifically, the heterocyclic group may be 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazinyl, dioxotriazinyl, pyrrolidinyl, piperidino, piperidinyl, pyranyl, thiopyranyl, 1,4-oxazinyl, morpholino, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl and phenoxazinyl.

These heterocyclic groups represented by $R^1$, $R^5$, $R^6$ and $R^9$ may have the same or different 1 to 5, preferably 1 to 2 substituents selected from, for example, a $C_{1-15}$alkyl group such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, pentadecyl, etc., a $C_{3-10}$cycloalkyl group such as cyclopropyl, cyclobutyl, cyclopentyl, cyclohexyl, etc., a $C_{2-10}$alkenyl group such as vinyl, allyl, 2-methylallyl, 2-butenyl, 3-butenyl, 3-octenyl, etc., a $C_{2-10}$alkynyl group such as ethynyl, 2-propynyl, 3-hexynyl, etc., a $C_{3-10}$cycloalkenyl group such as cyclopropenyl, cyclopentenyl, cyclohexenyl, etc., a $C_{6-10}$aryl group such as phenyl, naphthyl, etc., a $C_{7-11}$aralkyl group such as phenyl-$C_{1-5}$alkyl e.g. benzyl, phenylethyl, etc., nitro group, hydroxyl group, mercapto group, oxo group, thioxo group, cyano group, carbamoyl group, carboxyl group, a $C_{2-5}$alkoxycarbonyl group such as methoxycarbonyl, ethoxycarbonyl, etc., sulfo group, a halogen atom such as fluorine, chlorine, bromine, iodine, etc., a $C_{1-4}$alkoxy group such as methoxy, ethoxy, propoxy, isopropoxy, butoxy, isobutoxy, s-butoxy, t-butoxy, etc., a $C_{6-10}$aryloxy group such as phenoxy, etc., a $C_{1-4}$alkylthio group such as methylthio, ethylthio, propylthio, isopropylthio, butylthio, isobutylthio, s-butylthio, t-butylthio, etc., a $C_{6-10}$arylthio group such as phenylthio, etc., a $C_{1-4}$alkylsulfinyl group such as methylsulfinyl, ethylsulfinyl, propylsulfinyl, isopropylsulfinyl, butylsulfinyl, isobutylsulfinyl, s-butylsulfinyl, t-butylsulfinyl, etc., a $C_{6-10}$arylsulfinyl group such as phenylsulfinyl, etc., a $C_{1-4}$alkylsufonyl group such as methylsulfonyl, ethylsulfonyl, propylsulfonyl, isopropylsulfonyl, butylsulfonyl, isobutylsulfonyl, s-butylsulfonyl, t-butylsulfonyl, etc., a $C_{6-10}$arylsulfonyl group such as phenylsulfonyl, etc., amino group, a $C_{2-11}$carboxylic acylamino group such as acetylamino, propionylamino, benzoylamino, etc., a mono- or di-$C_{1-4}$alkylamino group such as methylamino, ethylamino, propylamino, isopropylamino, butylamino, dimethylamino, diethylamino, etc., a $C_{3-6}$cycloalkylamino group such as cyclohexylamino, etc., a $C_{6-10}$arylamino group such as anilino, etc., a $C_{1-11}$carboxylic acyl group such as formyl, acetyl, benzoyl, etc., and a 5- or 6-membered heterocyclic group containing 1 to 5, preferably 1 to 3 hetero atoms such as oxygen atom, sulfur atom and nitrogen atom or its condensed heterocyclic group such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl 3- 4- or 5-pyrazolyl, 2-, 4- or 5-imidazolyl, 3-, 4- or 5-isoxazolyl, 3-, 4- or 5-isothiazolyl, 1,2,3- or 1,2,4-triazolyl, 2-, 4- or 5-pyrimidinyl, benzothiazolyl, benzoxazolyl, triazinyl, pyrrolidinyl, piperidino, piperidinyl, morpholinyl, morpholino, benzimidazolyl, quinolyl, isoquinolyl, etc. Among these substituents, the aryl, aralkyl, cycloalkyl, cycloalkenyl, aryloxy, arylthio, arylsulfinyl, arylsulfonyl, arylamino and heterocyclic group may further have 1 to 5 substituents such as halogen atoms as mentioned above, hydroxyl group, nitro group, cyano group, $C_{1-4}$alkyl groups (e.g., methyl, ethyl, propyl, isopropyl, butyl, isobutyl, s-butyl, t-butyl, etc.), $C_{2-4}$alkenyl groups (e.g., vinyl, allyl, etc.), $C_{2-4}$alkynyl groups (e.g., ethynyl, 2-propynyl, etc.), phenyl group, $C_{1-4}$alkoxy groups, phenoxy group, $C_{1-4}$alkylthio groups as exemplified before and phenylthio group; and also the alkyl, alkenyl, alkynyl, alkoxy, alkylthio, alkylsulfinyl, alkylsulfonyl, amino, alkylamino and cycloalkylamino group may further have 1 to 5 substituents such as halogen atoms, a hydroxyl group, $C_{1-4}$alkoxy group and $C_{1-4}$alkylthio group as mentioned above.

The hydrocarbon group of the "hydrocarbon group which may be substituted" represented by $R^2$, $R^3$, $R^4$, $R^5$, $R^6$, $R^7$, $R^8$ and $R^9$ includes the $C_{1-15}$alkyl group, $C_{3-10}$cycloalkyl group, $C_{2-10}$ alkenyl group, $C_{2-10}$alkynyl group, $C_{3-10}$cycloalkenyl group, $C_{6-10}$aryl group and $C_{7-11}$aralkyl group as exemplified in the above as substituents on the heterocyclic group represented by $R^1$ and the like. Preferred alkyl groups are the ones having 1 to 6 carbon atoms.

These "hydrocarbon group which may be substituted" may have the same or different 1 to 5, preferably 1 to 3 substituents as exemplified in the above as substituents on the heterocyclic group represented by $R^1$ and the like.

The cyclic amino group formed by $R^3$ and $R^4$, or $R^7$ and $R^8$ with the adjacent nitrogen atom may be, for example, aziridino, azetidino, pyrrolidino, piperidino, morpholino, thiomorpholino, or the like. These cyclic amino groups may have substituents, preferably 1 to 3 substituents as exemplified before for the heterocylcic group represented by $R^1$ and the like.

The electron attractive group represented by X may be a cyano group, nitro group, a $C_{2-5}$alkoxycarbonyl group such as methoxycarbonyl, ethoxycarbonyl, etc., carboxyl group, a $C_{7-11}$aryloxycarbonyl group such as phenoxycarbonyl, etc., a heterocycle-oxycarbonyl group such as pyridyloxycarbonyl, thienyloxycarbonyl, etc., a $C_{1-4}$alkylsulfonyl group which may be substituted by halogen atoms, etc. such as methylsulfonyl, ethylsulfonyl, trifluoromethylsulfonyl, etc., sulfamoyl group, a $C_{1-4}$dialkoxyphosphoryl group such as diethoxyphosphoryl, etc., a $C_{2-4}$carboxylic acyl group which may be substituted by halogen atoms, etc., such as acetyl, trichloroacetyl, trifluoroacetyl, etc., carbamoyl group, or a $C_{1-4}$alkylsulfonylthiocarbamoyl group such as methylsulfonylthiocarbamoyl, etc.

The lower alkyl group represented by $R^{10}$ may be the $C_{1-4}$alkyl group as exemplified before, and preferably a methyl group.

Suitable examples of $R^1$ are 5- or 6-membered nitrogen containing heterocyclic groups, which may be substituted, such as pyridyl and thiazolyl. A preferable substituent of these heterocyclic groups is a halogen atom.

The symbol n is 0 or 1, and preferably 1.

Preferable examples of $R^2$, $R^3$ and $R^4$ are a hydrogen atom, a $C_{1-3}$alkyl group such as methyl, ethyl, propyl, etc. and a $C_{2-4}$carboxylic acyl group which may be substituted by a halogen atom such as formyl, acetyl, trifluoroacetyl, etc., among which a hydrogen atom and the $C_{1-3}$alkyl group are more preferable. A preferable example of X is the nitro group.

The moiety of

is, in some cases, preferably an electron donative group. Y is more preferably a hydroxyl group, a $C_{1-6}$alkylthio group or a $C_{6-10}$arylthio group, and $R^5$ is more preferably hydrogen or a $C_{1-3}$alkyl which may be substituted by one to three halogen atoms. Especially, the compounds [I] wherein Y is a $C_{1-6}$alkylthio or $C_{6-10}$arylthio group and $R^5$ is a hydrogen atom and the compounds [I] where Y is hydroxyl group and $R^5$ is trichloromethyl group are preferable.

Accordingly, preferable compounds [I] are those where $R^1$ is a pyridyl or thiazolyl group which may be substituted, $R^2$, $R^3$ and $R^4$ may be the same or different and represent a hydrogen atom or a $C_{1-3}$ alkyl group, $R^5$ is hydrogen or a $C_{1-6}$alkyl group which may be substituted by halogen atoms, X is a nitro group, n is 1, and Y is a hydroxyl group, a group of the formula $-NR^{7'}R^{8'}$ (in which $R^{7'}$ and $R^{8'}$ are each a $C_{1-3}$alkyl group or $R^{7'}$ and $R^{8'}$ are combined to form a pyrrolidinyl group with the adjacent nitrogen atom) or a group of the formula $-SR^9$ (in which $R^9$ is the same as above).

Especially preferable compounds [I] are those where $R^1$ is a pyridyl or thiazolyl group substituted with a halogen, $R^2$, $R^3$ and $R^4$ are each a hydrogen atom or a $C_{1-3}$alkyl group, $R^5$ is a hydrogen atom or trichloromethyl group, n is 1, X is a nitro group and Y is a hydroxyl group, a $C_{1-6}$alkylthio group or a $C_{6-10}$aryl group.

There exist usually cis-isomers and trans-isomers of the diaminoethylene compounds [I] resulting from the double bond and in some cases stereoisomers due to $R^1$, $R^2$, $R^3$, $R^4$, $R^5$ and Y and mixtures thereof and they are included in the scope of the present invention, even though one of the cis and trans isomers is shown in this specification.

Examples of the salts of the diaminoethylene compounds [I] include the salts with an inorganic acid such as hydrochloric acid, hydrobromic acid, hydroiodic acid, phosphoric acid, sulfuric acid, perchloric acid, etc., or with an organic acid such as formic acid, acetic acid, tartaric acid, malic acid, citric acid, oxalic acid, succinic acid, benzoic acid, picric acid, methanesulfonic acid, p-toluenesulfonic acid, etc.

The diaminoethylene compound [I] or a salt thereof can be used as an insecticidal composition in a conventional form of emulsifiable concentrate, oily preparation, wettable powder, dust, granule, tablet, spray or ointment which may be prepared by dissolving or dispersing one or more kinds of the compounds [I] or salts thereof in a proper liquid carrier or by mixing or absorbing one or more kinds of the compounds [I] or salts thereof with or on a proper solid carrier. These preparations can be prepared by any known method, and an emulsifying agent, suspending agent, spreading agent, penetrating agent, wetting agent, thickening agent and/or stabilizer may be added to the preparation, if necessary. A surface active agent exemplified below can be used as the emulsifying agent, dispersing agent and penetrating agent, and Dyne ® (Trademark, manufactured by Takeda Chemical Industries, Ltd.) and the surface active agent exemplified below can be used as the spreading agent.

The amount of the active ingredient to be incorporated in the insecticidal composition is variable in accordance with the purpose. The suitable proportion is usually about 1 to 90% by weight, preferably about 5 to 70% by weight, on the basis of the entire composition in the case of emulsifiable concentrates or wettable powders, about 0.1 to 10% by weight, on the same basis in the case of oil solutions or dusts, and about 0.1 to 20% by weight, preferably about 0.1 to 10% by weight, on the same basis in the case of granules. However, such concentration may properly be changed in accordance with the purpose of use. The emulsifiable concentrates, wettable powders or the like are suitably diluted and extended (for example to 100-100,000 times) with water or the like on the occasion of use, and then scattered.

Suitable liquid carriers (solvents) to be used is, for example, water, alcohols such as methanol, ethanol, propanol, isopropanol, ethylene glycol, etc., ketones such as acetone, methyl ethyl ketone, etc., ethers such as dioxane, tetrahydrofuran, ethylene glycol monomethyl ether, diethylene glycol monomethyl ether, propylene glycol monomethyl ether, etc., aliphatic hydrocarbons such as kerosine, kerosene, fuel oil, machine oil, etc., aromatic hydrocarbons such as benzene, toluene, xylene, solvent naphtha, methylnaphthalene, etc., halogenated hydrocarbons such as dichloromethane, chloroform, carbon tetrachloride, etc., acid amides such as N,N-dimethylformamide, N,N-dimethylacetamide, etc., esters such as ethyl acetate, butyl acetate, fatty acid glycerol esters, etc., nitriles such as acetonitrile, propionitrile, etc., or the like. These liquid carriers can be used individually or as a suitable mixture thereof.

Suitable solid carriers (diluents or extenders) are, for example, vegetable powders such as soybean flour, tobacco flour, wheat flour, sawdust, etc., mineral powders such as clays (e.g. kaolin, bentonite, acid clay), talcs (e.g. talc powder, pyrophyllite powder), silicas (e.g. diatomaceous earth, mica powder), etc., calcium carbonate, alumina, sulfur powders, active carbon, or the like. These solid carriers can be used individually or as a suitable mixture thereof.

Suitable bases for the ointment are, for example, polyethylene glycol, pectin, polyalcohol esters of higher aliphatic acids such as glycerin mono-stearate, etc., cellulose derivatives such as methyl cellulose, etc., sodium alginate, bentonite, higher alcohols, polyalcohols such as glycerin, etc., vaseline, white petrolatum, liquid paraffin, lard, various kinds of vegetable oils, lanolin, dehydrated lanolin, hardened oil, resins, or the like. These bases can be used individually or as a mixture thereof, or together with surface active agents exemplified in the following.

Suitable surface active agents to be used as the emulsifying agent, spreading agent, penetrating agent or dispersing agent are, for example, nonionic or anionic surface active agents such as soaps: polyoxyethylene alkyl aryl ethers [e.g. Noigen ® E.A 142 ® from Dai-ichi Kogyo Seiyaku K.K., Japan, Nonal ® from Toho Chemical, Japan]; alkyl sulfates [e.g. Emal 10 ®, Emal 40 ® from Kao K.K. Japan]; alkyl sulfonates [e.g. Neogen ®, Neogen T ® from Dai-ichi Kogyo Seiyaku K.K., Neopellex ® from Kao K.K.]; polyethylene glycol ethers [e.g. Nonipol 85 ®, Nonipol 100 ®, Nonipol 160 ® from Sanyo Kasei K.K., Japan]; polyhydric alcohol esters [e.g. Tween 20 ®, Tween80 ® from Kao K.K], or the like.

The diaminoethylene compounds [I] and their salts can be used in combination with other insecticides (e.g. pyrethroid insecticides, organophosphorus insecticides, carbamate insecticides, natural insecticides, etc.), acaricides, nematicides, herbicides, plant hormones, plant growth regulators, fungicides (e.g., copper fungicides, organic chlorine fungicides, organic sulfur fungicides, phenol fungicides, etc.), synergistic agents, attractants, repellents, pigments and/or fertilizers.

The diaminoethylene compound [I] and salts thereof are effective in the control of household pests and animal or plant parasitizing insects, and exhibit strong pesticidal effects when brought into contact with the host animals or plants by direct application thereto. The most remarkable feature of the diaminoethylene compound [I] and their salts are, however, that they display potent pesticidal effects even after they have been absorbed into plants via the root, leaf, stem or the like and come into contact with the pests as the pests suck or gnaw at the plants. This property is advantageous in the control of sucking or biting insects. Furthermore, the compounds [I] and their salts produce less damage to plants and possess low toxicity against fishes, and accordingly they have safe and advantageous properties as a sanitary, horticultural and agricultural pesticide.

The insecticidal compositions containing a diaminoethylene compound [I] or salt thereof are particularly effective in the control of the following kinds of pests, for example: pests of the order Hemiptera such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis gossypii,* etc., pests of the order Lepidoptera such as *Spodoptera litura, Plutella xylostella, Pieris rapae crucivora, Chilo suppressalis, Autographa nigrisigna, Helicoverpa assulta, Pseudaletia separata, Mamestra brassicae, Adoxophyes orana fasciata, Notarcha derogata, Cnaphalocrocis medinalis, Phthorimaea operculella,* etc., pest of the order Cleoptero such as *Epilachna vigintioctopunctata, Aulacophora femoralis, Phyllotreta striolata, Oulema oryzae, Echinocnemus squameus,* etc., pests of the order Diptera such as *Musca domestica, Culex pipiens pallens, Tabanus trigonus, Delia antiqua, Delia platura,* etc., pests of the order Orthoptera such as *Locusta migratoria, Gryllotalpa africana,* etc., pests of the order Dictyoptera such as *Blattella germanica, Periplaneta fuliginosa,* etc., pests of the order Tetranychidae such as *Tetranychus urticae, Panonychus citri, Tetranychus kanzawai, Tetranychus cinnabarinus, Panonychus ulmi, Aculops pelekassi,* etc., nematodes such as *Aphelenchoides besseyi,* and the like.

The insecticidal compositions of the present invention are excellent agricultural chemicals having fairly low toxicity and good safety. The compositions can be used in a way similar to a conventional insecticidal composition and can exert excellent effects in comparison with the conventional composition. For example, the insecticidal compositions of the present invention can be applied to the target insects, by treatment in a nursery box, application to stem and leaf of crop, spraying for insects, application in water of a paddy field or soil treatment of a paddy field. While the amount of application may broadly vary depending on the season, place and method of applicaton, and so forth, the active ingredient (diaminoethylene compound [I] or its salt) is used, in general, in an amount of 0.3 g to 3,000 g, preferably 50 g to 1,000 g per hectare. When the insecticidal composition of this invention is in a form of a wettable powder, it can be used by diluting it so as to be 0.1 to 1,000 ppm, preferably 10 to 500 ppm as the final concentration of the active ingredient.

The diaminoethylene compounds [I] and their salts can be prepared by the aforementioned methods (A) to (H). The methods are described in further detail below. When the compound [I] is obtained in a free form in the following methods, said compound can be converted to a salt as exemplified before, and when the compound[I] is obtained in the form of a salt, said salt can be converted to a free compound by a conventional method. When a kind of the compounds [I] is used as a starting material for preparing another kind of compounds [I], the starting compound can be used in a free or salt form. In case the other starting materials can exist in the form of a salt as mentioned before, said starting compounds can also be used in a free or salt form. Therefore, starting compounds and products in the following methods include their salts as exemplified for the compounds [I].

(A) A compound [$I^a$] can be prepared by reacting a compound [II] with a compound [III]. The compound [III] can be used in an amount of 2 to 20 molar equivalents, preferably 0.8 to 2.0 equivalents to the compound [II].

The reaction may be conducted without a solvent, but it is usually carried out in a proper solvent. The solvent may be, for example, water, alcohols such as methanol, ethanol, propanol, isopropanol, etc., aromatic hydrocarbons such as benzene, toluene, xylene, etc., halogenated hydrocarbons such as dichloromethane, chloroform, carbon tetrachloride, etc., saturated hydrocarbons such as hexane, heptane, cyclohexane, etc., ethers such as diethyl ether, tetrahydrofuran (hereinafter abbreviated as THF), dioxane, etc., ketones such as acetone, methyl ethyl ketone, etc., nitriles such as acetonitrile, propionitrile, etc., sulfoxides such as dimethyl sulfoxide (hereinafter abbreviated as DMSO), etc., acid amides such as N,N-dimethylformamide (hereinafter abbreviated as DMF), N,N-dimethylacetamide, etc., esters such as ethyl acetate, butyl acetate, etc., and carboxylic acids such as acetic acid, propionic acid, etc. These solvents can be used individually or, if necessary, in a mixture of two or more kinds thereof, in a proportion of 1:1 to 1:10. In case the reaction mixture is not homogenous, the reaction may be carried out in the presence of a phase transfer catalyst, for example, quaternary ammonium salts such as triethylbenzylammonium chloride, tri-n-octylmethylammonium chloride, trimethyldecylammonium chloride, tetramethylammonium bromide, etc., crown ethers, or the like.

This reaction can be carried out in the presence of an acidic or basic substance. The acidic substance may be, for example, hydrohalogenic acids such as hydrochloric acid, hydrobromic acid, etc., phosphoric acid, lower carboxylic acids such as acetic acid, propionic acid, etc., sulfonic acids such as methanesulfonic acid, p-toluenesulfonic acid, etc., and the acidic substance is usually used in an amount of 0.01 to 10 equivalents to the compound [II]. The basic substance may be, for example, inorganic bases such as sodium bicarbonate, potassium bicarbonate, sodium carbonate, potassium carbonate, sodium hydroxide, potassium hydroxide, calcium hydroxide, phenyl lithium, butyl lithium, sodium methoxide, sodium ethoxide, metallic sodium, metallic potassium, etc., or organic bases such as triethylamine, tributylamine, N,N-dimethylaniline, pyridine, lutidine, collidine, 4-(dimethylamino)-pyridine, 1,8-diazabicyclo[5,4,0]-undecene-7 (hereinafter abbreviated as DBU), etc., and such basic substances are usually used in an amount of 0.01 to 20 equivalents to the compound [II]. The above organic bases can be used as a solvent, too. This reaction is usually carried out at 20° to 100° C., and may occasionally be conducted under heating to about 200° C., and sometimes it is conducted advantageously under high pressure (2 to 100 atmospheric pressure). The reaction time is usually 30 minutes to 50 hours, preferably 2 to 20 hours.

(B) A compound [$I^b$] can be prepared by reacting a compound [II], compound [III] and compound [IV]. The compound [III] and compound [IV] are preferably used in an amount of 0.8 to 2 equivalents to the compound [II] respectively, but in an amount up to 10 equivalents to the compound [II] respectively unless they interfere with the reaction. However, when the compound [IV] is ammonia or a primary amine, the compound [III] is preferably used in an amount of 0.8 to 1.5 molar equivalents to the compound [II].

This reaction can be carried out without solvent or in a solvent as exemplified in the above method (A). When the reaction mixture is not homogeneous, the reaction may be carried out in the presence of a phase transfer catalyst as mentioned in the method (A), and it may advantageously be carried out in the presence of an acidic substance as mentioned in the method (A). The reaction temperature and reaction time can be those used in the method (A).

(C) A compound [I] can be prepared by reacting a compound [V] with a compound [VI]. The compound [VI] is preferably used in an amount of 0.8 to 1.5 equivalents to the compound [V], and it can be used in an amount of 1.5 to 10 equivalents unless an impediment to the reaction is caused.

This reaction can be carried out without solvent or in a solvent as mentioned in the method (A). When the reaction mixture is not homogeneous, the reaction can be conducted in the presence of a phase transfer catalyst as mentioned in the method (A).

This reaction may be accelerated by addition of a base or a metal salt in an amount of 0.01 to 10 equivalents, preferably 0.01 to 3 equivalents, to the compound [V]. The bases to be added may be the inorganic base or organic base as mentioned in the method (A), and the organic base can be used as a solvent, too. The metal salts may be, for example, copper salts such as copper chloride, copper bromide, copper acetate, copper sulfate, etc., mercury salts such as mercury chloride, mercury nitrate, mercury acetate, etc., or the like.

The reaction temperature of this reaction is usually −20° to 150° C. and the reaction time is 10 minutes to 50 hours, and preferably they are 0° to 100° C. and 1 to 20 hours, respectively.

(D) A compound [I] can also be prepared by reacting a compound [VII] with a compound [VIII]. The conditions for this reaction are similar to those mentioned in the above method (C).

(E) A compound [$I^d$] can be prepared by oxidizing a compound [$I^c$] which is included in the object compounds of this invention. The oxidizing agent may be, for example, peracids such as hydrogen peroxide, peracetic acid, perbenzoic acid, m-chloroperbenzoic acid, etc., sodium methaperiodate, t-butylhydroperoxide, ozone, selenium dioxide, chromic acid, acetyl nitrate, benzoyl nitrate, iodine, bromine, N-bromosuccinimide (NBS), iodosylbenzene, the combination of sulfuryl chloride and hydrous silica gel, t-butyl hypochlorite, dinitrogen tetroxide, or the like. The reaction is usually carried out in a solvent as mentioned in the method (A).

These oxidizing agents are preferably used in an amount of 0.8 to 1.2 equivalents to the compound [I$^c$] when m' in the compound [I$^d$] is 1, and 2 to 5 equivalents when m' is 2. However, the oxidizing agent can if indicated be used in a large excessive amount.

When m' in the compound [I$^d$] is 2, the corresponding compound [I$^d$] wherein m' is 1, namely, a compound of the formula:

$$R^1-(CH_2)_n-N(R^2)\diagdown C=C \diagup X \diagdown CH-S(O)R^9 \diagup R^5 \text{ with } R^3-N(R^4) \text{ branch} \quad [I^e]$$

wherein each symbol has the same meaning as above, is produced in this reaction procedure, and then the resultant compound is further oxidized to give a compound [I$^d$] (m'=2). Therefore, the intermediated compound [I$^e$] may be isolated and then reacted with an oxidizing agent to give a compound [I$^d$].

The reaction temperature and reaction time are usually in a range of 0° C. to 100° C. and 10 minutes to 10 hours, though they vary in accordance with the kind of the oxidizing agent to be used.

(F) A compound [I] can also be prepared by reacting a compound of the formula:

$$H-N(R^2)\diagdown C=C \diagup X \diagdown CH-Y \diagup R^5 \text{ with } R^3-N(R^4) \text{ branch} \quad [IX]$$

wherein each symbol has the same meaning as above, with a compound of the formula:

$$R^1-(CH_2)n-Z \quad [X]$$

wherein each of R$^1$ and n has the same meaning as above, and Z is a leaving group.

The leaving group represented by Z in the compound [X] may be, for example, a halogen atom such as chlorine, bromine, etc., a C$_{1-4}$alkylsulfonyloxy group which may be substituted with 1-3 halogen atoms such as methanesulfonyloxy, trifluoromethanesulfonyloxy, etc., an C$_{6-10}$arylsulfonyloxy group such as benzenesulfonyloxy, p-toluenesulfonyloxy, etc., or the like.

The compound [X] is preferably used in an amount of 0.8 to 1.5 equivalents to the compound [IX]. However, it may be used in a large excess amount, unless an impediment to the reaction is caused.

This reaction can be accelerated by using a base as mentioned in the method (A). The base can be used in an amount of 0.5 to 10 equivalents, preferably 0.8 to 1.5 equivalents to the compound [IX]. When an organic base is used as a base, it can be used as a solvent, too.

This reaction is preferably carried out in a solvent as mentioned in the method (A). When the reaction mixture is not homogeneous, a phase transfer catalyst as mentioned in the method (A) may be used.

The reaction temperature is usually −20° to 150° C., preferably 0° to 80° C., and the reaction time is usually 10 minutes to 50 hours, preferably 2 to 20 hours.

(G) A compound [I] can also be prepared by reacting a compound of the formula:

$$R^1-(CH_2)_n-N(R^{2a})\diagdown C=C \diagup X \diagdown CH-Y \diagup R^5 \text{ with } R^{3a}-N(R^{4a}) \text{ branch} \quad [I^f]$$

wherein each of R$^1$, R$^5$, n, X and Y has the same meaning as above, and R$^{2a}$, R$^{3a}$ and R$^{4a}$ are same or different each being a hydrogen atom or a hydrocarbon group which may be substituted, or R$^{3a}$ and R$^{4a}$ are combined to form a cyclic amino group together with the adjacent nitrogen atom, provided that at least one of R$^{2a}$, R$^{3a}$ and R$^{4a}$ is a hydrogen atom, with a compound of the formula:

$$R-Z \quad [XI]$$

wherein, R is a hydrocarbon group which may be substituted, and Z has the same meaning as above.

The "hydrocarbon group which may be substituted" for R, R$^{2a}$, R$^{3a}$ and R$^{4a}$ is the same as those exemplified before for R$^2$, R$^3$ and R$^4$, and the "cyclic amino group" formed by R$^{3a}$ and R$^{4a}$ with the adjacent nitrogen atom, is the same as those exemplified before for R$^3$ and R$^4$. According to this reaction the hydrogen atom(s) for R$^{2a}$, R$^{3a}$ and/or R$^{4a}$ is (are) replaced by the hydrocarbon group(s) which may be substituted.

This reaction can be carried out under similar conditions as in the method (F).

(H) A compound [I$^b$] can also be prepared by reacting a compound [I$^a$] which is included in the object compounds of this invention with a compound [IV]. The compound [IV] is preferably used in an amount of 0.8 to 2 equivalents to the compound [I$^a$]. However, it can be used in a large excess amount to about 10 equivalents, unless an impediment to the reaction is caused.

Thus obtained compounds [I] and their salts can be isolated and purified by conventional methods such as concentration, concentration under reduced pressure, distillation, fractional distillation, extraction with solvent, chromatography, crystallization, recrystallization, or the like.

Among the compounds used as the starting materials in the above methods, the compounds [II], [VI] and [X] are known compounds described in European Patent Publication 302,389, and they can be prepared by processes described therein. Compounds [III], [IV], [VIII] and [XI] are also known compounds, and they are available on the market or can be prepared in accordance with known methods. Compounds [V] and compounds [VII] are novel, and can be prepared, for example, by the methods shown in the following [scheme 1] and [scheme 2].

[Scheme 1]

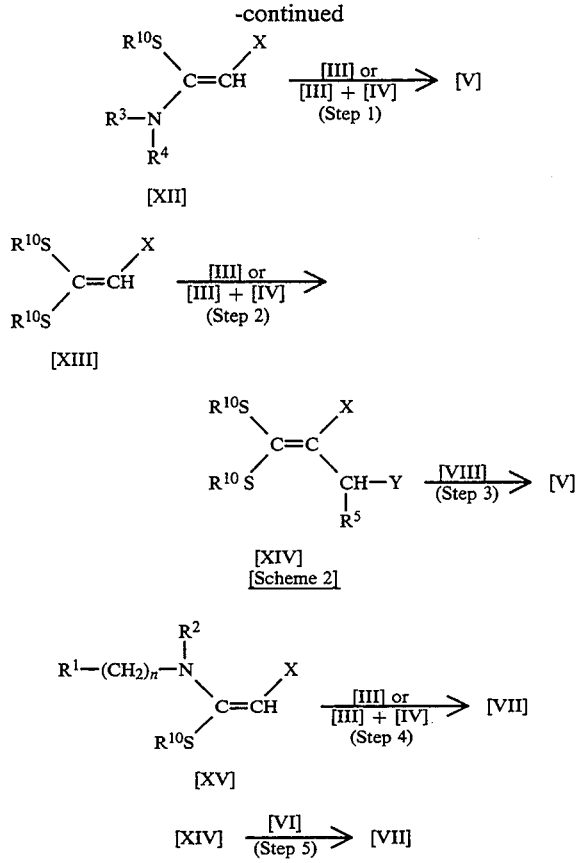

[wherein each symbol has the same meaning as above]

Method of Scheme 1:

(Step 1) A compound [V] can be prepared by reacting a compound [XII] with a compound [III], or a compound [XII] with a compound [III] and a compound [IV] using the conditions of the method (A) or (B) mentioned before.

(Step 2) A compound [XIV] can be prepared by reacting a compound [XIII] with a compound [III], or a compound [XIII] with a compound [III] and a compound [IV] under similar conditions to the aforementioned method (A) or (B).

(Step 3) A compound [V] can be prepared by reacting a compound [XIV] with a compound [VIII] in accordance with conditions mentioned in the above method (C).

Method of Scheme 2:

(Step 4) A compound [VII] can be prepared by reacting a compound [XV] with a compound [III], or a compound [XV] with a compound [III] and a compound [IV] in accordance with conditions mentioned in the aforementioned method (A) or (B).

(Step 5) A compound [VII] can be prepared by reacting a compound [XIV] with a compound [VI] under conditions mentioned in the aforementioned method (C).

The starting compounds [XII], [XIII] and [XV] used in the methods of the above Scheme 1 and Scheme 2 are known compounds, and they are available on the market or can be prepared by the methods described in European Patent Publication 302,389.

Compounds [I$^c$] and [I$^f$] are included in the object compounds of this invention, and they can be prepared by the methods (A) to (H). Compounds [IX] can be prepared by methods of the aforementioned methods (A) to (E), (G) or (H).

The starting compounds [I$^c$], [I$^e$], [I$^f$], [II], [V], [VII], [IX], [XII] and [XV] can exist in a form cis- or trans-isomer or a mixture thereof, each of which can be used as starting material. However, one of the isomers is shown in this specification.

The diaminoethylene derivatives [I] and their salts possess excellent insecticidal activity as shown in the following tests.

Test 1

Effect against *Nilaparvata lugens*

Five mg of each test compound (shown by the Compound No. in the following Examples) was dissolved in 0.5 ml of acetone containing Tween 20 ® and diluted to a concentration of 500 ppm by addition of Dyne ® (a spreader produced by Takeda Chemical Industries, Ltd. of Japan) diluted 3000 times with tap water. The solution at a rate of 10 ml/pot was sprayed on leaf and stem of rice seedlings at the second leaf stage developed in a nursery paper pot. The treated rice seedlings were put into a test tube containing tap water at the bottom, to which ten larvae at the third instar of *Nilaparvata lugens* were released. After being sealed with an aluminum stopper, the test tube was kept in an incubator adjusted to 25° C. Dead larvae were counted seven days after the release. The mortality was calculated by the following formula, and the results are shown in Table 1.

$$\text{Mortality } (\%) = \frac{\text{the number of dead insects}}{\text{the number of insects released}} \times 100$$

TABLE 1

| Compound No. | Mortality Rate (%) |
|---|---|
| 1 | 100 |
| 2 | 100 |
| 3 | 100 |
| 4 | 100 |
| 5 | 100 |
| 6 | 100 |
| 8 | 100 |
| 11 | 100 |
| 12 | 100 |
| 13 | 100 |
| 15 | 100 |
| 16 | 100 |
| 18 | 100 |
| 19 | 100 |
| 21 | 100 |
| 22 | 100 |
| 23 | 100 |
| 24 | 100 |
| 26 | 100 |
| 29 | 100 |
| 30 | 100 |
| 31 | 100 |
| 32 | 100 |
| 33 | 100 |
| 35 | 100 |
| 39 | 100 |
| 40 | 100 |
| 41 | 100 |
| 42 | 100 |
| 45 | 100 |
| 48 | 100 |
| 49 | 100 |
| 50 | 100 |
| 54 | 100 |

As shown in the above Table 1, the diaminoethylene derivatives [I] and their salts possess an excellent insecticidal effect against *Nilaparvata lugens*.

Test 2

Effect against *Aphis gossypii*

Five mg of each test compound (shown by Compound No. obtained in the following Examples) was dissolved in 0.5 ml of acetone containing Tween 20 ® and diluted to a concentration of 100 ppm by addition of Dyne ® diluted 3000 times with tap water. The solution, at a rate of 10 ml/pot, was sprayed on leaf and stem of cucumber seedlings developed at the first leaf stage, to which ten female imagos of *Aphis gossypii* were released one day before the application of the spray. The test plant was kept in a glass incubator adjusted to 27° C., and the number of living female imagos was counted two days after the treatment. The mortality rate was calculated by the following formula, and the results are shown in Table 2.

$$\text{Mortality Rate (\%)} = \frac{\left(\begin{array}{c}\text{the number}\\ \text{of released}\\ \text{female imagos}\end{array}\right) - \left(\begin{array}{c}\text{the number}\\ \text{of living}\\ \text{female imagos}\end{array}\right)}{\text{the number of released female imagos}} \times 100$$

TABLE 2

| Compound No. | Mortality Rate (%) |
| --- | --- |
| 1 | 100 |
| 2 | 100 |
| 3 | 100 |
| 4 | 100 |
| 6 | 100 |
| 11 | 100 |
| 12 | 100 |
| 15 | 100 |
| 16 | 100 |
| 18 | 100 |
| 19 | 100 |
| 21 | 100 |
| 22 | 100 |
| 23 | 100 |
| 24 | 100 |
| 26 | 100 |
| 29 | 100 |
| 30 | 100 |
| 31 | 100 |
| 32 | 100 |
| 35 | 100 |
| 39 | 100 |
| 41 | 100 |
| 42 | 100 |
| 45 | 100 |
| 48 | 100 |
| 49 | 100 |
| 50 | 100 |
| 54 | 100 |

As shown in the above Table 2, the diaminoethylene derivatives [I] and their salts possess an excellent insecticidal effect against *Aphis gossypii*.

The following Examples are given for illustrating the present invention in more detail, and accordingly it should be noted that the present invention is not restricted by these Examples.

The elution of column chromatography in the Examples was conducted under observation of thin layer chromatography (TLC). The TLC observation was carried out by using Kieselgel 60F$_{254}$® (70 to 230 mesh) (manufactured by Merck Co.) as a TLC plate, the same solvent as the one used as an eluting solvent in the column chromatography as a developing solvent, and a UV detector as a detecting means. Silica gel for the column was Kieselgel 60 ® (70 to 230 mesh) (manufactured by Merck Co.). NMR spectra representing proton NMR, were measured using tetramethylsilane as an internal standard and Varian EM 390 (90 MHz) as a spectrometer, and all δ values are shown by ppm. When a mixed solvent was used as a developing solvent, the mixing rate is shown by the volume in a parenthesis.

The symbols used in the following Examples and Table 3 have the following meanings, respectively.

Me: methyl group, Et: ethyl group, n-Pr: n-propyl group, i-Pr: isopropyl group, t-Bu: t-butyl group, Ph: phenyl group, S: singlet, br: broad, d: doublet, dd: double doublet, t: triplet, q: quartet, m: multiplet, J: coupling constant, Hz: Hertz, CDCl$_3$: deuterochloroform, %: weight %, room temperature: about 15° to 25° C.

EXAMPLE 1

A mixture of 1-[N-(6-chloro-3-pyridylmethyl)-N-methylamino]-1-methylamino-2-nitroethylene(0.39 g), 37% aqueous solution of formaldehyde (0.16 g), 50% aqueous solution of dimethylamine (0.18 g) and acetonitrile (3 ml) was stirred at room temperature for 8.5 hours. The reaction mixture was concentrated to give 1-[N-(6-chloro-3-pyridylmethyl)-N-methylamino]-3-dimethylamino-1-methylamino-2-nitro-propene (Compound No. 1) (0.49 g) as a syrupy liquid.

NMR(CDCl$_3$): 2.26(6H,s), 2.7–3.1(6H,m), 3.44(2H,s), 4.51(2H,s), 6.00(1H,br,s), 7.34(1H,d,J=8.5Hz), 7.72(1H,dd,J=8.5,2.5Hz), 8.33 (1H,d,J=2.5Hz)

EXAMPLE 2

Chloral hydrate (0.40 g) was added slowly in 40 minutes to a mixture of 1-[N-(6-chloro-3-pyridylmethyl)-N-methylamino]-1-methylamino-2-nitroethylene (0.26 g), triethylamine (0.1 g) and acetonitrile (3 ml). The mixture was stirred at room temperature for 21 hours and under refluxing for 9 hours. The resultant crystals were collected by filtration to give 1,1,1-trichloro-4-[N-(6-chloro-3-pyridylmethyl)-N-methylamino]-4-methylamino-3-nitro-3-buten-2-ol (Compound No. 11) (0.23 g) as a white solid.

EXAMPLE 3

A mixture of 1-[N-(6-chloro-3-pyridylmethyl)-N-ethylamino]-1-methylamino-2-nitroethylene (2.71 g), p-chlorothiophenol (1.45 g), 37% aqueous solution of formaldehyde (0.97 g) and ethanol (30 ml) was stirred at 20° C. for 2 hours and under refluxing for 5 hours. The reaction mixture was concentrated and the residue was purified by column chromatography (eluting solvent:dichloromethane-methanol (6:1) to give 3-(4-chlorophenylthio)-1-[N-(6-chloro-3-pyridylmethyl)-N-ethylamino]-1-methylamino-2-nitro-1-propene (Compound No. 31) (3.30 g) as a yellow amorphous.

NMR(CDCl$_3$): 1.10(3H,t,J=7.0Hz), 2.96(3H,s), 3.2–3.7(2H,m), 4.14(2H,s), 4.72(2H,br,s), 7.15–7.5(5H,m), 7.66(1H,dd,J=8.5,2.5Hz), 8.32(1H,d,J=2.5Hz), 9.90(1H,br,s)

The compounds No. 1 to 54 shown in the following Table 3 can be prepared by the methods described in the above Examples or aforementioned in this specification. The compounds obtained in the above Examples are also listed in Table 3.

TABLE 3

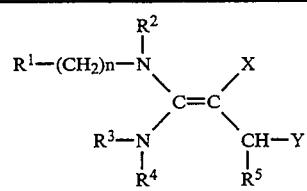

| Compound No. | R¹ | n | R² | R³ | R⁴ | R⁵ | X | Y | Form |
|---|---|---|---|---|---|---|---|---|---|
| 1 | 2-Cl-pyridin-5-yl | 1 | Me | Me | H | H | $NO_2$ | $NMe_2$ | syrup |
| 2 | 2-Cl-pyridin-5-yl | 1 | Et | Me | Me | H | $NO_2$ | (azetidin-1-yl) | syrup |
| 3 | 2-Cl-pyridin-5-yl | 1 | i-Pr | Me | H | H | $NO_2$ | $NHCH_2CF_3$ | amorphous |
| 4 | 2-Cl-thiazol-5-yl | 1 | H | Me | Me | H | $NO_2$ | OH | syrup |
| 5 | 2-(4-Cl-phenoxy)-pyridin-5-yl | 1 | Et | Me | H | H | $NO_2$ | OH | crystal |
| 6 | 2-Br-pyridin-5-yl | 1 | H | Me | H | $CCl_3$ | $NO_2$ | OH | amorphous |
| 7 | 2-Br-pyridin-5-yl | 1 | Me | Me | H | $CCl_3$ | $NO_2$ | OH | |
| 8 | 2-Br-pyridin-5-yl | 0 | H | Me | H | $CCl_3$ | $NO_2$ | OH | amorphous |
| 9 | 2-Cl-pyridin-5-yl | 1 | H | Me | Me | $CCl_3$ | $NO_2$ | OH | |
| 10 | 2-Cl-pyridin-5-yl | 1 | Me | H | H | $CCl_3$ | $NO_2$ | OH | |
| 11 | 2-Cl-pyridin-5-yl | 1 | Me | Me | H | $CCl_3$ | $NO_2$ | OH | crystal |

TABLE 3-continued $$R^1-(CH_2)_n-N(R^2)-C(=C(X)(CH(Y)R^5))-N(R^3)(R^4)$$

| Compound No. | R¹ | n | R² | R³ | R⁴ | R⁵ | X | Y | Form |
|---|---|---|---|---|---|---|---|---|---|
| 12 | 2-Cl-pyridin-5-yl | 1 | Et | Me | H | CCl₃ | NO₂ | OH | amorphous |
| 13 | 2-Cl-pyridin-5-yl | 0 | H | Me | H | CCl₃ | NO₂ | OH | amorphous |
| 14 | pyridin-3-yl | 0 | H | Me | Me | CCl₃ | NO₂ | OH | |
| 15 | 2-Cl-thiazol-5-yl | 1 | Me | Me | Me | CCl₃ | NO₂ | OH | syrup |
| 16 | 2-Cl-thiazol-5-yl | 1 | Et | Me | H | CCl₃ | NO₂ | OH | amorphous |
| 17 | 2-Br-thiazol-5-yl | 1 | Me | Me | H | CCl₃ | NO₂ | OH | |
| 18 | 2-Cl-pyridin-5-yl | 1 | H | Me | Me | H | NO₂ | S-Ph | amorphous |
| 19 | 2-Cl-pyridin-5-yl | 1 | Me | Me | Me | H | NO₂ | S-t-Bu | amorphous |
| 20 | 2-Cl-pyridin-5-yl | 1 | Me | H | H | H | NO₂ | S-cyclohexyl | |
| 21 | 2-Cl-pyridin-5-yl | 1 | Me | Me | H | H | NO₂ | S-(4-Me-C₆H₄) | amorphous |
| 22 | 2-Cl-pyridin-5-yl | 1 | Me | Me | H | H | NO₂ | S-(4-Cl-C₆H₄) | amorphous |

TABLE 3-continued
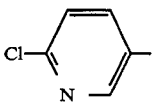
| Compound No. | R¹ | n | R² | R³ | R⁴ | R⁵ | X | Y | Form |
|---|---|---|---|---|---|---|---|---|---|
| 23 | 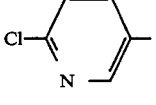 | 1 | Me | Me | H | H | $NO_2$ | S-Me | syrup |
| 24 | 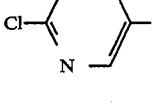 | 1 | Me | Me | H | H | $NO_2$ | S-Et | syrup |
| 25 | 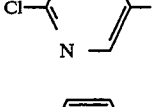 | 1 | Me | Me | H | H | $NO_2$ | S-n-Pr | |
| 26 | 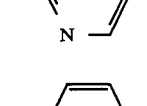 | 1 | Me | Me | H | H | $NO_2$ | S-t-Bu | amorphous |
| 27 | 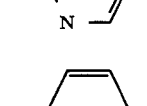 | 1 | Me | Et | H | H | $NO_2$ | S-i-Pr | |
| 28 | 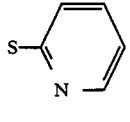 | 1 | Me | Me | H | H | $NO_2$ | 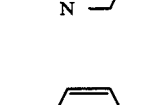 | |
| 29 | 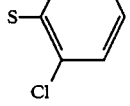 | 1 | Et | Me | H | H | $NO_2$ | 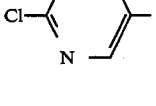 | amorphous |
| 30 | 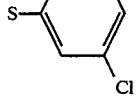 | 1 | Et | Me | H | H | $NO_2$ | 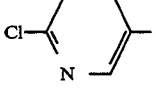 | amorphous |
| 31 | 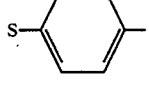 | 1 | Et | Me | H | H | $NO_2$ | 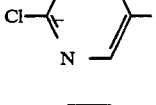 | amorphous |
| 32 | 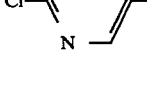 | 1 | Et | Me | H | H | $NO_2$ | S-t-Bu | amorphous |
| 33 | 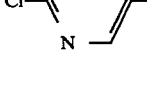 | 0 | H | Me | H | H | $NO_2$ | S-Ph | syrup |

TABLE 3-continued
$$R^1-(CH_2)_n-\underset{\underset{R^4}{|}}{\underset{R^3-N}{|}}\overset{R^2}{\underset{|}{N}}\,C=C\overset{X}{\underset{CH-Y}{\underset{|}{R^5}}}$$
| Compound No. | R¹ | n | R² | R³ | R⁴ | R⁵ | X | Y | Form |
|---|---|---|---|---|---|---|---|---|---|
| 34 | 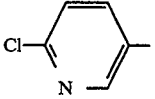 | 0 | H | Me | H | H | NO₂ | 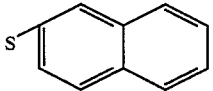 | |
| 35 | 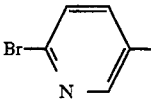 | 1 | Me | Me | H | H | NO₂ | S-t-Bu | amorphous |
| 36 | 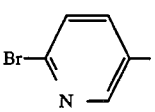 | 1 | Me | Me | H | H | NO₂ | S(O)-t-Bu | |
| 37 | 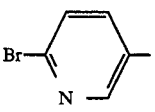 | 1 | Me | Me | H | H | NO₂ | S(O)₂-t-Bu | |
| 38 | 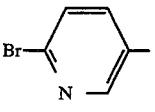 | 1 | Me | Me | H | H | NO₂ | S-CH₂Ph | |
| 39 | 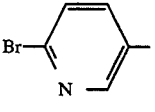 | 1 | Et | Me | H | H | NO₂ | 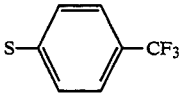 | syrup |
| 40 | 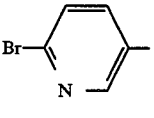 | 0 | H | Me | H | H | NO₂ | 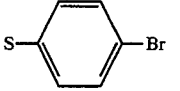 | syrup |
| 41 | 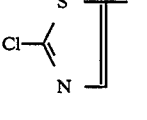 | 1 | H | Me | H | H | NO₂ | S-n-Pr | syrup |
| 42 | 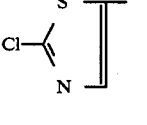 | 1 | Me | Me | H | H | NO₂ | 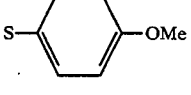 | syrup |
| 43 | 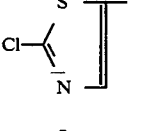 | 1 | Me | Me | H | H | NO₂ | SCH₂CH₂OH | |
| 44 | 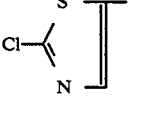 | 1 | Et | H | H | H | NO₂ | 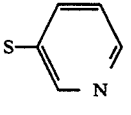 | |

TABLE 3-continued $$R^1-(CH_2)_n-\underset{\underset{R^4}{|}}{\underset{R^3-N}{|}}\underset{R^2}{\overset{|}{N}}\underset{}{C}=C\underset{CH-Y}{\overset{X}{\diagdown}}\underset{R^5}{|}$$

| Compound No. | R¹ | n | R² | R³ | R⁴ | R⁵ | X | Y | Form |
|---|---|---|---|---|---|---|---|---|---|
| 45 | Cl-thiazole | 1 | Et | Me | H | H | NO₂ | S-Et | syrup |
| 46 | Br-thiazole | 1 | Me | Me | H | H | NO₂ | SCH₂Ph | |
| 47 | Br-thiazole | 1 | Me | Me | H | H | NO₂ | S-Me | |
| 48 | 3-pyridyl | 1 | H | Me | H | H | NO₂ | S—CH₂—C₆H₄—Cl | amorphous |
| 49 | 3-pyridyl | 1 | Me | Me | H | H | NO₂ | S—C₆H₄—t-Bu | amorphous |
| 50 | 3-pyridyl | 1 | Et | Me | H | H | NO₂ | S-t-Bu | amorphous |
| 51 | 3-pyridyl | 1 | n-Pr | Me | H | H | NO₂ | S-t-Bu | |
| 52 | 3-pyridyl | 0 | H | Me | H | H | NO₂ | S-i-Pr | |
| 53 | 3-pyridyl | 0 | H | Me | H | H | NO₂ | S—C₆H₄—Me | |
| 54 | 3-pyridyl | 0 | H | Me | Me | H | NO₂ | S-Et | syrup |

1) mp: 150–160° C. (decomp.)
2) mp: 155–159° C. (decomp.)

EXAMPLE 4

Compound No. 31 (20 weight %), xylene (75 weight %) and polyoxyethylene glycol ether (Nonipole 85 ®) (5 weight %) were mixed well to give an emulsifiable concentrate.

EXAMPLE 5

Compound No. 11 (30 weight %), sodium lignin sulfonate (5 weight %), polyoxyethylene glycol ether (Nonipole 85 ®) (5 weight %), white carbon (30 weight %) and clay (30 weight %) were mixed well to give wettable powders.

EXAMPLE 6

Compound No. 5 (3 weight %), white carbon (3 weight %) and clay (94 weight %) were mixed well to give a dust.

EXAMPLE 7

Compound No. 45 (10 weight %), sodium lignin sulfonate (5 weight %) and clay (85 weight %) were pulverized and mixed. Water was added to the mixture, which was kneaded, granulated and dryed to give granules.

The present invention contributes to agriculture by providing excellent insecticides.

What we claimed is:

1. A diaminoethylene compound of the formula:

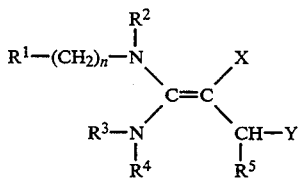
[I]

wherein $R^1$ is a heterocyclic group which may be substituted; $R^2$, $R^3$ and $R^4$ may be the same or different and are a hydrogen atom or a hydrocarbon group which may be substituted, or $R^3$ and $R^4$ are combined to form a cyclic amino group together with the adjacent nitrogen atom; $R^5$ is a hydrogen atom, a hydrocarbon group which may be substituted or a heterocyclic group which may be substituted; n is 0 or 1, X is an electron attractive group; Y is a group of the formula —$OR^6$ (in which $R^6$ is a hydrogen atom, a hydrocarbon group which may be substituted or a heterocyclic group which may be substituted), a group of the formula —$NR^7R^8$ (in which $R^7$ and $R^8$ are the same or different, a hydrogen atom or a hydrocarbon group which may be substituted, or $R^7$ and $R^8$ are combined to form a cyclic amino group with the adjacent nitrogen atom), or a group of the formula: —$S(O)_mR^9$ (in which $R^9$ is a hydrocarbon group which may be substituted or a heterocyclic group which may be substituted, and m is 0, 1 or 2) or its salt.

2. A compound of claim 1 in which the moiety of

forms an electron donative group.

3. A compound of claim 1 in which Y is a hydroxyl group, a $C_{1-6}$alkylthio group or a $C_{6-10}$arylthio group and $R^5$ is a hydrogen atom or a $C_{1-3}$alkyl group which may be substituted by one to three halogen atoms.

4. A compound of claim 1 in which Y is a $C_{1-6}$alkylthio group or a $C_{6-10}$arylthio group and $R^5$ is a hydrogen atom, or Y is a hydroxyl group and $R^5$ is a trichloromethyl group.

5. A compound of claim 1 in which $R^1$ is a pyridyl or thiazolyl group which may be substituted.

6. A compound of claim 1 in which $R^1$ is a pyridyl or thiazolyl group which is substituted by a halogen atom.

7. A compound of claim 1 in which $R^2$, $R^3$ and $R^4$ being the same or different are a hydrogen atom or a $C_{1-3}$alkyl group.

8. A compound of claim 1 in which X is a nitro group.

9. A compound of claim 1 in which n is 1.

10. A compound of claim 1 in which $R^1$ is a pyridyl or thiazolyl group which may be substituted; $R^2$, $R^3$ and $R^4$ being the same or different are a hydrogen atom or a $C_{1-3}$alkyl group; X is a nitro group; $R^5$ is a hydrogen atom or a $C_{1-3}$alkyl group which may be substituted by one to three halogen atoms; Y is a hydroxyl group, a group of the formula —$NR^{7'}R^{8'}$ ($R^{7'}$ and $R^{8'}$ being the same or different are a $C_{1-3}$alkyl group or are combined to form a pyrrolidyl group together with the adjacent nitrogen atom) or a group of the formula —$SR^9$ ($R^9$ has the same meaning as defined in claim 1); and n is 1.

11. A compound of claim 1 in which $R^1$ is a pyridyl or thiazolyl group substituted with a halogen, $R^2$, $R^3$ and $R^4$ being the same or different are a hydrogen atom or a $C_{1-3}$alkyl group, $R^5$ is a hydrogen atom or trichloromethyl group, n is 1, X is a nitro group and Y is a hydroxyl group, a $C_{1-6}$alkylthio group or a $C_{6-10}$arylthio group.

12. A compound of claim 1 wherein Y is —OH and $R^5$ is —$CCl_3$.

13. A compound of claim 1 wherein Y is —$SR^9$ and $R^5$ is Hydrogen.

14. The compound of claim 1 which is 1,1,1,-trichloro-4-[N-(6-chloro-3-pyrimidylmethyl)-N-ethylamino]-4-methylamino-3-nitro-3-buten-2-ol.

15. The compound of claim 1 which is 1,1,1,-trichloro-4-[N-(6-chloro-3-pyridylmethyl)-N-methylamino]-4-methylamino-3-nitro-3-buten-2-ol.

16. The compound of claim 1 which is 1,1,1,-trichloro-4-[N-(2-chloro-5-thiazolylmethyl)-N-ethylamino]-4-methylamino-3-nitro-3-buten-2-ol.

17. The compound of claim 1 which is 1-(2-chloro-5-thiazolylmethylamino)-1-methylamino-2-nitro-3-(n-propylthio)-1-propene.

18. A compound of the formula:

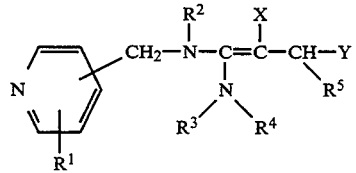

wherein
$R^1 = C_{1-15}$ alkyl, $C_{3-10}$ cycloalkyl, $C_{2-10}$ alkenyl, $C_{2-10}$ alkynyl, nitro, cyano, halogen, $C_{1-4}$ alkoxyl, $C_{1-4}$ alkylthio;
$R^2$ = hydrogen, a hydrocarbon selected from $C_{1-15}$ alkyl or $C_{3-10}$ cycloalkyl;
$R^3$ = hydrogen, $C_{1-6}$ alkyl or $C_{3-6}$ cycloalkyl;
$R^4$ = hydrogen, $C_{1-15}$ alkyl, $C_{3-6}$ cycloalkyl or $C_{6-10}$ aryl;
$X = NO_2$;
$Y = OH$;
$R^5 = C_{1-3}$ alkyl which is substituted by one to three halogens, and the salts with inorganic acids.

19. A diaminoethylene compound of the formula:

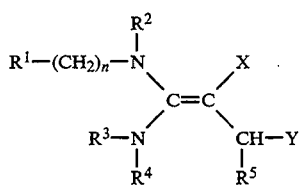

wherein $R^1$ is a pyridyl or thiazolyl group which may be substituted; $R^2$, $R^3$ and $R^4$ may be the same or different and are a hydrogen atom or a hydrocarbon group which may be substituted, or $R^3$ and $R^4$ are combined to form a cyclic amino group together with the adjacent nitrogen atom; $R^5$ is a $C_1$-$C_6$ alkyl group which is substituted by halogen atoms; n is 0 or 1, X is a —$NO_2$ group; Y is a group of the formula —$OR^6$, in which $R^6$ is a hydrogen atom, a hydrocarbon group which may be substituted, or a heterocyclic group which may be substituted, or Y is a group of the formula —$S(O)_m R^9$ in which $R^9$ is a hydrocarbon group which may be substituted or a heterocyclic group which may be substituted, and m is 0, 1 or 2 or its salt.

20. An insecticidal composition comprising an effective insecticidal amount of a compound of claim 1 or its salt and a carrier or diluent.

21. A method of killing insects which comprises applying to said insects an effective amount of a compound of claim 1.

* * * * *